United States Patent

Moszner et al.

Patent Number: 6,136,887
Date of Patent: Oct. 24, 2000

[54] VINYLCYCLOPROPANE-(METH)ACRYLATES AND THEIR USE

[75] Inventors: Norbert Moszner, Eschen; Volker Rheinberger, Vaduz, both of Liechtenstein; Thomas Voelkel, Lindau, Germany; Urs Karl Fischer, Arbon, Switzerland

[73] Assignee: Ivoclar AG, Liechtenstein

[21] Appl. No.: 09/266,509

[22] Filed: Mar. 11, 1999

Related U.S. Application Data

[60] Provisional application No. 60/099,564, Sep. 9, 1998.

[30] Foreign Application Priority Data

Mar. 17, 1998 [DE] Germany ............ 198 12 888

[51] Int. Cl.$^7$ ............. A61K 6/083; C07C 69/743
[52] U.S. Cl. ............. 523/116; 523/118; 524/558; 524/559; 526/308; 526/309; 260/998.11; 433/228.1; 560/124; 560/125; 560/220; 564/190
[58] Field of Search ............ 560/124, 125, 560/220; 523/116, 118; 524/558, 559; 526/308, 309; 260/998.11; 433/228.1; 564/190

[56] References Cited

U.S. PATENT DOCUMENTS 5,886,212   3/1999   Rheinberger et al.

FOREIGN PATENT DOCUMENTS 0 798 286 A1   3/1997   European Pat. Off.

*Primary Examiner*—Andrew E. C. Merriam
*Attorney, Agent, or Firm*—Nixon Peabody LLP

[57] ABSTRACT

The invention relates to vinylcyclopropane derivatives according to the formula

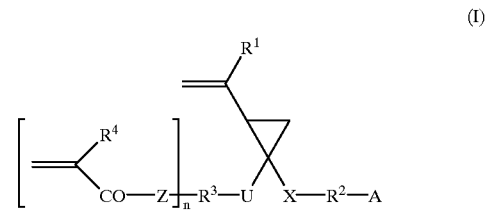

in which A is $-[-Y-CO-C(=CH_2)R^4]_m$ or $-C(=CH_2)CO-O-C_{1-4}$-alkyl, U and X, independently of each other, stand for CO, COO or CONH; Y and Z stand for O or NH or are absent, but Y and Z cannot be absent at the same time; n, m stand for a whole number from 0 to 4, but n and m are not 0 at the same time; $R^1$ is H, $CH_3$ or Cl; $R^2$, $R^3$ stand for H, a $C_1$- to $C_{10}$-alkyl or alkylene radical, which can be interrupted by O, S or NH, for a $C_6$- to $C_{14}$-aryl or arylene, $C_7$- to $C_{14}$-alkylaryl or alkylarylene or a $C_5$- to $C_8$-cycloalkyl or cycloalkylene radical; and $R^4$ is H or a $C_1$- to $C_{10}$-alkyl radical, and to processes for their production. The compounds are suitable in particular for the production of adhesives, cements, composites and mouldings.

11 Claims, No Drawings

VINYLCYCLOPROPANE-(METH) ACRYLATES AND THEIR USE

This application claims priority benefit of U.S. Patent Application Serial No. 60/099,564, filed on Sep. 9, 1998, which is hereby incorporated by reference.

The invention relates to vinylcyclopropane derivatives having polymerizable (meth)acrylate radicals, processes for their production and dental materials on the basis of these compounds.

1,1-disubstituted 2-vinylcyclopropanes have attracted interest because of their small shrinkage during radical polymerization. F. Sanda, T. Takata, T. Endo, Macromolecules 26 (1993) 1818) have shown e.g. that the liquid monomers 1,1 bis(ethoxy-carbonyl)- or 1,1-dicyano-2-vinylcyclopropane produce a small volume shrinkage during polymerization compared with conventional vinyl monomers, such as e.g. acrylonitrile or methyl methacrylate.

J. Sugiyama, K. Ohashi, M. Ueda, Macromolecules 27 (1994) 5543 even observed an expansion in volume during the radical polymerization of 1,1-bis(phenoxycarbonyl)-2-vinylcyclo-propane. However, a disadvantage with the known vinylcyclopropanes is their small polymerization capacity. During the copolymerization of 1,1-bis (ethoxycarbonyl)-2-vinylcyclopropane with methyl methacrylate (MMA) for example only heterogeneously composed products are obtained with a small tying-in of the vinylcyclopropane derivative into the copolymer structure (F. Sanda, T. Takata, T. Endo, Macromolecules 27 (1994) 3982), so that the mechanical properties of the polymers are only unsatisfactory.

In addition, vinylcyclopropanes with several groups capable of polymerization are known. F. Sanda, T. Takata, T. Endo, Macromolecules 27 (1994), 3986 describe 1-vinyl-5,7-dioxaspiro[2.5]octan-6-one, a hybrid monomer which contains a vinylcyclopropane group and a cyclic carbonate group, and T. Okazaki, F. Sanda, T. Endo, Macromolecules 28 (1995) 6026, describe 1,10-bis(vinyl)-4,8,12,15-tetraoxatrispiro[2.2.2.2.2.2]pentadecane, a monomer in which two vinylcyclopropane groups are connected to each other via a spiroacetal unit. These compounds are sensitive to hydrolysis and, compared with monofunctional vinylcyclopropanes, do not display an improved radical polymerization capacity with (meth)acryl compounds.

Hybrid monomers which also contain a (meth)acrylate group alongside a vinylcyclopropane group are not known.

The object of the invention is to provide polymerizable vinylcyclopropanes which display a low volume shrinkage during polymerization and at the same time are satisfactorily radically copolymerizable with acrylates or methacrylates.

This object is surprisingly achieved by hybrid vinylcyclo-propane methacrylates according to the general formula (I), in which U, X, Y, Z, $R^1$, $R^2$, $R^3$, $R^4$, n and m, independently of one another, have the following meanings:

(I)

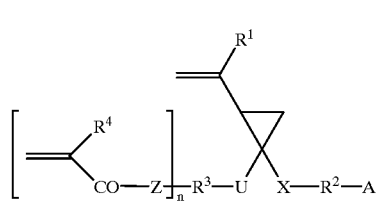

A —[—Y—CO—C(=$CH_2$)$R^4$]$_m$ or —C(=$CH_2$)CO—O—$C_{1-4}$-alkyl, alkyl being preferably methyl or ethyl;

U, X CO, COO or CONH;

Y, Z O, NH or are absent, but Y and Z cannot be absent at the same time when A is —[—Y—CO—C(=$CH_2$)$R^4$]$_m$;

n, m a whole number from 0 to 4, but n and m are not 0 at the same time;

$R^1$ H, $CH_3$ or Cl;

$R^2$, $R^3$ H, $C_1$- to $C_{10}$-alkyl or alkylene, which can be interrupted by O, S or NH, $C_6$- to $C_{14}$-aryl or arylene, $C_7$- to $C_{14}$-alkylaryl or alkylarylene or $C_5$- to $C_8$-cycloalkyl or cycloalkylene; and $R^4$ H or a $C_1$- to $C_{10}$-alkyl.

Preferred definitions which can be chosen independently of one another are:

A —[—Y—CO—C(=$CH_2$)$R^4$]$_m$;

U, X COO or CONH, in particular COO,

Y, Z O or is absent, n, m an integer from 0 to 2, derivatives in which n=1 or 2 and m=0 being particularly preferred, $R^1$ H, $R^2$, $R^3$ $C_1$- to $C_6$-alkyl or alkylene, $C_6$-aryl or arylene or $C_6$-cycloalkyl or cycloalkylene, in particular $C_1$- to $C_3$-alkyl or alkylene, phenyl or phenylene, in particular p-phenylene, cyclohexyl or cyclohexylene, in particular p-cyclohexylene and/or $R^4$ H, $C_1$–$C_3$-alkyl, in particular $CH_3$.

Vinylcyclopropane derivatives in which $R^2$ and $R^3$ are the same, $R^4$ is H, n, m are in each case 1 and U, X stand for COO or CONH, or $R^2$ and $R^3$ are different, $R^4$ is H, n is 0, m is 1 or 2, Z is absent and Y stands for O are particularly preferred.

The other substituents and indices have the meanings given above.

Quite particularly preferred vinylcyclopropane (meth) acrylates of formula (I) are:

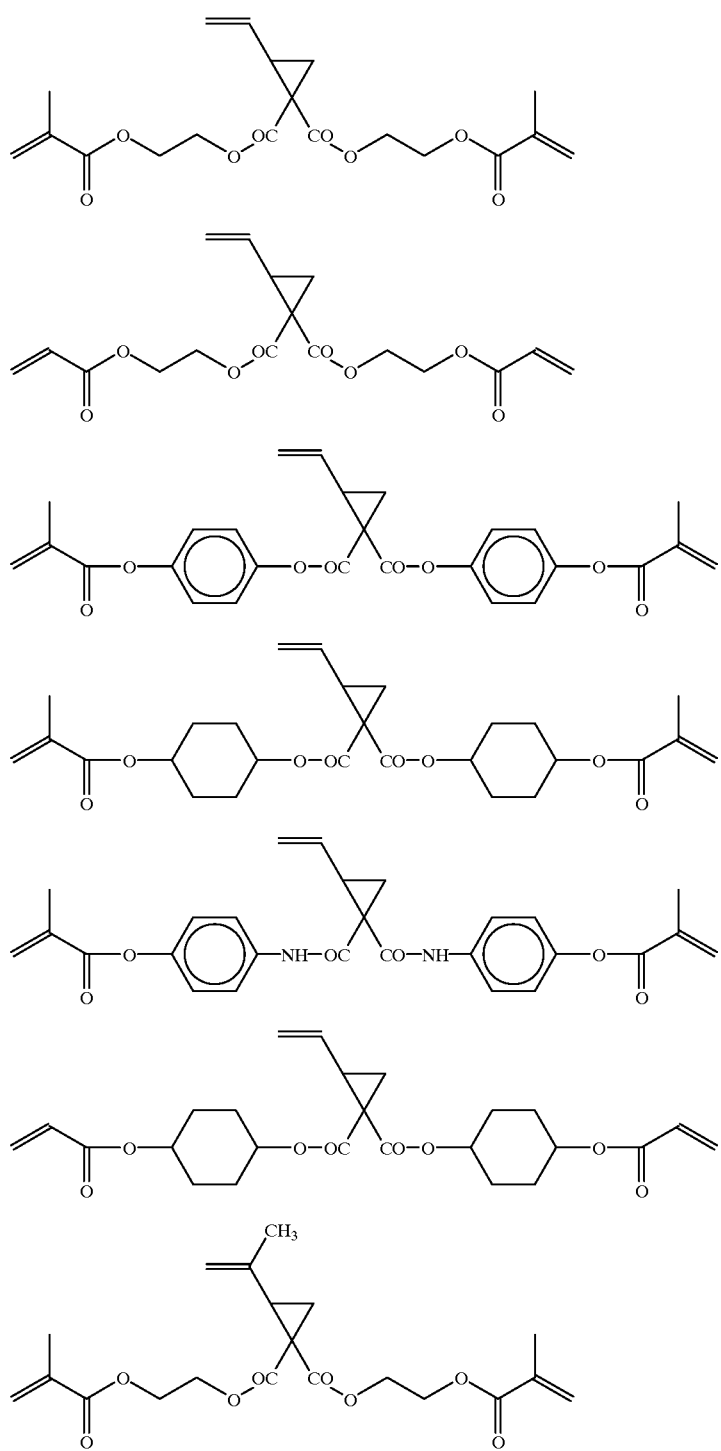

-continued

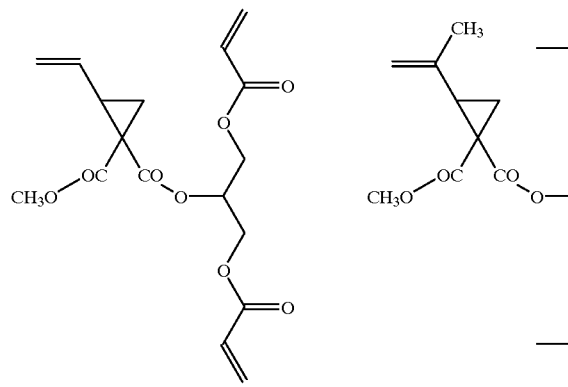

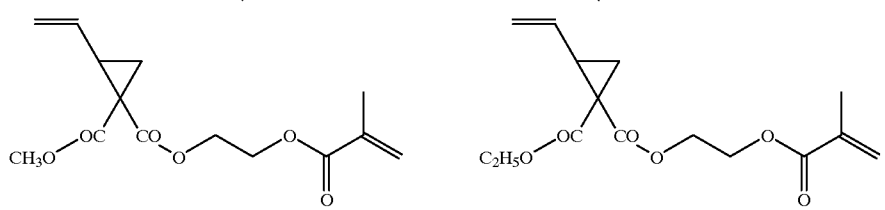

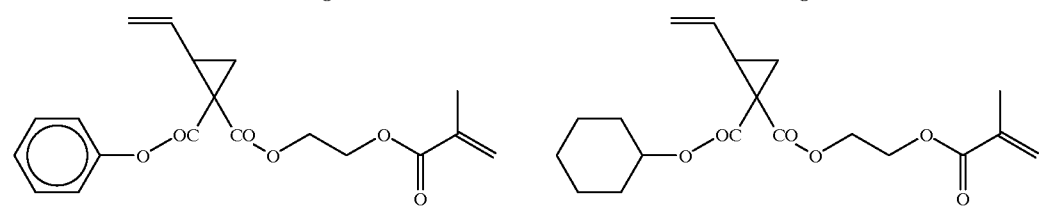

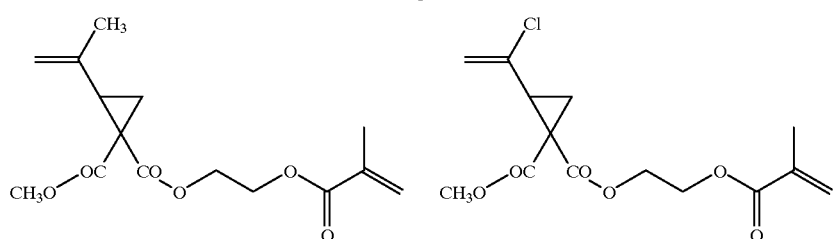

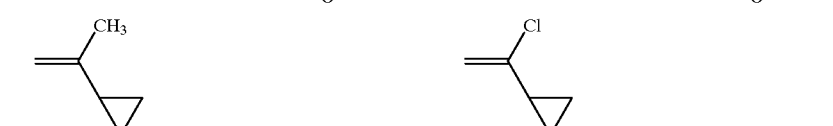

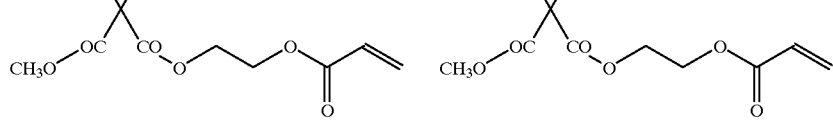

The vinylcyclopropane (meth)acrylates (I) according to the invention can be produced by reacting vinylcyclopropane derivatives of formula (II) stepwise with (meth)acrylic acid derivatives (III), in which W stands for OH or halogen, preferably Br or Cl, to give the intermediate products (IV) which are then converted with further (meth)acrylic acid derivative (III) into the desired vinylcyclopropane derivatives. If the (meth)-acrylic acid derivative (III) used in the second reaction step is identical with that used in the first step, symmetrical vinylcyclopropane-(meth)acrylates are obtained, while unsymmetrical compounds (I) are accessible through the use of a differently structured derivative (III).

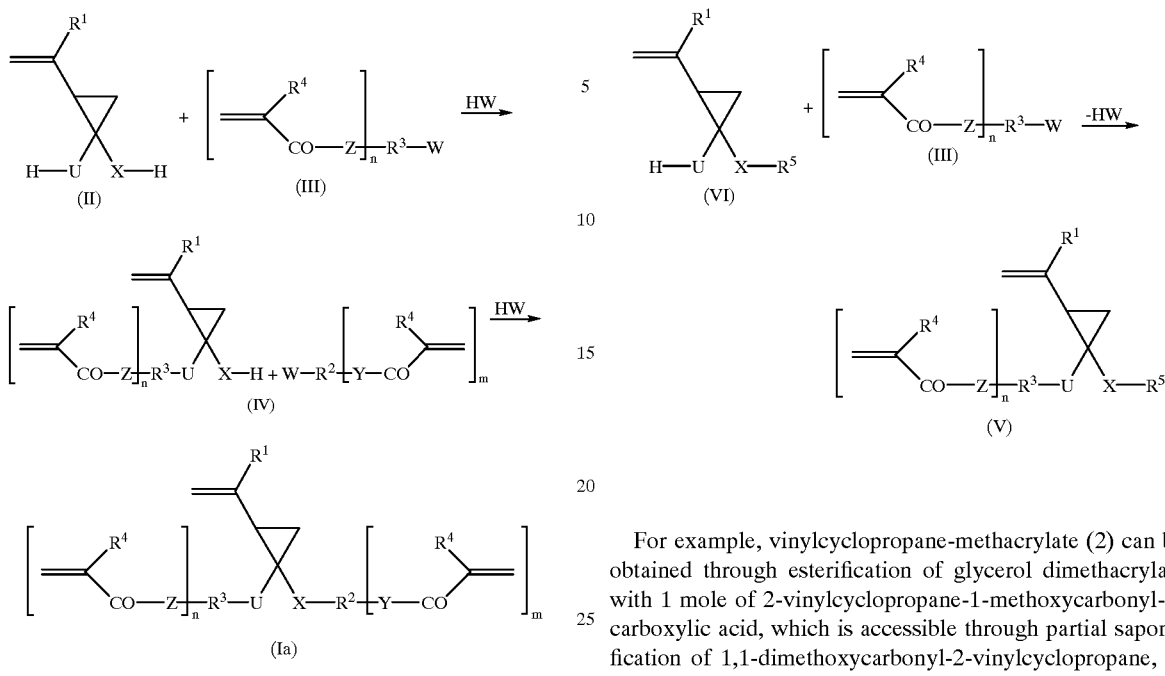

For example, vinylcyclopropane-methacrylate (1) can be obtained through esterification of 2 moles of 2-hydroxyethyl meth-acrylate (HEMA) with 1 mole of 2-vinylcyclopropane-1,1-dicarboxylic acid, which is accessible through saponification of 1,1-dimethoxycarbonyl-2-vinylcyclopropane, in the presence of dicyclohexylcarbodiimide (DCC).

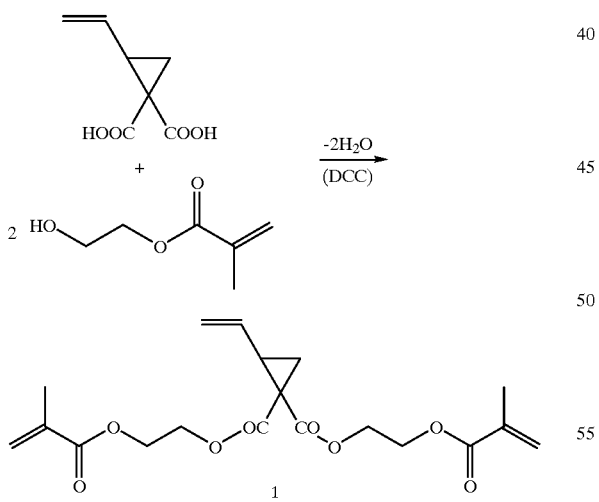

Vinylcyclopropane-(meth)acrylates in which n or m stand for 0 can be produced by reacting unsymmetrically substituted 2-vinylcyclopropane derivatives (VI), in which $R^5$ is preferably a $C_1$- to $C_{10}$-alkyl or phenyl radical, analogously with 1 mole of (meth)acrylic acid derivative (III) to give the vinylcyclopropane-(meth)acrylates (V).

For example, vinylcyclopropane-methacrylate (2) can be obtained through esterification of glycerol dimethacrylate with 1 mole of 2-vinylcyclopropane-1-methoxycarbonyl-1-carboxylic acid, which is accessible through partial saponification of 1,1-dimethoxycarbonyl-2-vinylcyclopropane, in the presence of dicyclohexylcarbodiimide (DCC).

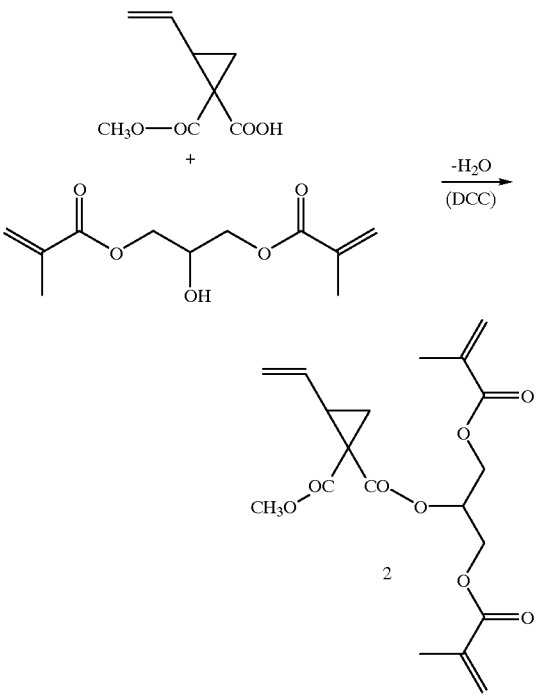

The compounds of formula (II) can be produced analogously to the processes known for the production of vinylcyclopropanes (cf. e.g. U.S. Pat. No. 4,713,478 and U.S. Pat. No. 4,713,479) through reaction of trans-1,4-dibromobut-2-enes which are unsubstituted ($R^1$=absent) or substituted in 2-position with corresponding malonic acid derivatives, recourse to the protective groups technique possibly being necessary.

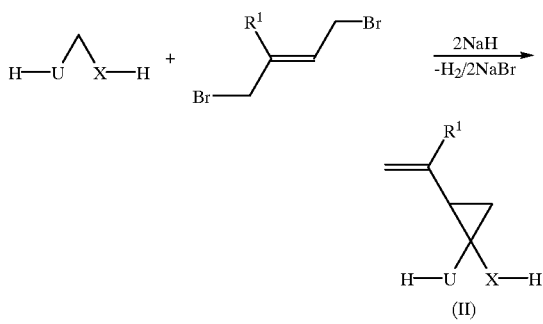

(II)

Known OH— or NH$_2$-group-containing (meth)acryl compounds can be used as (meth)acryl derivatives (III). Preferred compounds are 2-hydroxyethyl (meth)acrylate, 2-hydroxypropyl (meth)acrylate, glycerol di(meth)acrylate, oligomeric ethylene glycol mono(meth)acrylates, 3-hydroxyphenyl (meth)acrylate, 4-hydroxy-benzyl (meth)acrylate, 4-hydroxycyclohexyl (meth)acrylate, 2-aminoethyl (meth)acrylate, 4-aminophenyl (meth)acrylate or triethylenediaminomono(meth)acrylate.

Such (meth)acryl educts can be easily obtained e.g. by reacting known di- or polyhydric alcohols, di- or multifunctional amino compounds or amino alcohols which contain at least a number of p OH or NH$_2$ groups in the molecule, p being $\geq 2$, with (p–1) mole of (meth)acrylic acid chloride or anhydride or are accessible by reacting r moles of glycidyl (meth)acrylate with compounds which contain r OH—, NH$_2$ or COOH-groups per molecule, r being $\geq 1$.

The vinylcyclopropane derivatives according to the invention are particularly suitable for the production of adhesives, composites, cements or mouldings, such as e.g. lenses or plates, in particular for the production of dental materials.

For this, the monomers according to the invention are mixed with an initiator for the radical polymerization and preferably also with additional monomers, fillers and optionally other auxiliaries.

During polymerization, because of their hybrid monomer structure, the compounds according to the invention produce either linear poly[(meth)acrylates] with lateral 2-vinylcyclopropane groups or crosslinked polymers.

The known initiators for cold, hot and photocuring are suitable as initiators for the radical polymerization. Suitable initiators are described for example in the Encyclopedia of Polymer Science and Engineering, Vol. 13, Wiley-Intersci. Pub., New York etc. 1988, p. 754 et seq.

Preferred initiators are azo-compounds, such as azobis(isobutyronitrile) (AIBN) or azobis(4-cyanovaleric acid) or peroxides, such as dibenzoyl peroxide, dilauroyl peroxide, tert.-butyl peroctoate, tert.-butyl perbenzoate or di-(tert.-butyl)-peroxide.

Benzpinacol and 2,2'-di(C$_1$–C$_8$-alkyl)benzpinacols are particularly suitable as initiators for hot curing.

Suitable photoinitiators for the UV or visible range are described by J. P. Fouassier, J. F. Rabek (Pub.), Radiation Curing in Polymer Science and Technology, Vol. II, Elsevier Applied Science, London and New York 1993, pages 155 to 237. Preferred photoinitiators are benzoin ethers, dialkyl benzil ketals, dialkoxyacetophenones, acylphosphinic oxides, α-diketones, such as 10-phenanthrenequinone, diacetyl, furil, anisil, 4,4'-dichlorobenzil and 4,4'-dialkoxybenzil and camphor quinone.

Dibenzoyl peroxide, camphor quinone and acylphosphinic oxides are preferred for the production of dental materials.

Preferred additional monomers for producing adhesives or dental materials are crosslinking bi- or multifunctional acrylates or methacrylates, such as e.g. bisphenol-A-di (meth)acrylate, bis-GMA, an addition product from methacrylic acid and bisphenol-A-diglycidyl ether, 7,7,9-trimethyl-4,13-dioxo-3,14-dioxa-5,12-diazahexadecan-1, 16-diyl-dimethacrylate (UDMA), an addition product from hydroxyethyl methacrylate and 2,2,4-trimethylhexamethylene diisocyanate, di-, tri- or tetraethylene glycol di(meth)acrylate, decanediol di(meth)acrylate, trimethylolpropane tri(meth)acrylate, pentaerythritol tetra (meth)acrylate, butanediol di(meth)acrylate, 1,10-decanediol di(meth)acrylate, 1,12-dodecanediol di(meth) acrylate, which are accessible by esterification of (meth) acrylic acid with the corresponding diols, as well as di- and multifunctional 2-vinyl-cyclopropane derivatives which are accessible by reacting 1-methoxycarbonyl-2-vinylcyclopropane-1-carboxylic acid with di- or polyvalent OH— or NH$_2$— compounds as coupling component, i.e. e.g. with ethylene glycol, di- or triethylene glycol, butylene glycol, 1,6-hexanediol, glycerol, triethanolamine, trimethylolpropane triol, pentaerythritol or glucose, as well as hydroquinone, resorcinol, pyrocatechol or pyrogallol, ethylene diamine, propylene diamine, hexamethylene diamine, o-, p- or m-phenylene diamine.

All organic and inorganic particles or fibres are suitable as fillers for the improvement of the mechanical properties.

Preferred fillers for producing dental materials such as fixing cements or filling composites are amorphous, spherical materials based on mixed oxides from SiO$_2$, ZrO$_2$ and/or TiO$_2$ with a mean average particle size of 0.005 to 2.0 μm, preferably 0.1 to 1 μm, as are disclosed for example in DE-PS 32 47 800, microfine fillers such as pyrogenic silica or precipitation silica as well as macro- or mini-fillers, such as quartz, glass ceramic or glass powders with an average particle size of 0.01 to 20 μm, preferably 0.5 to 5 μm, as well as X-ray-opaque fillers such as ytterbium trifluoride. Mini-fillers are taken to be fillers with a particle size of 0.5 to 1.5 μm, and macro-fillers to be fillers with a particle size of 10 to 20 μm. Glass fibres, polyamide or carbon fibres can also be used.

The compositions according to the invention can also contain further auxiliaries if needed, in particular stabilizers, UV absorbers, dyes, pigments and/or slip agents. Stabilizers are taken to be substances which prevent premature polymerization and thus above all increase the storage stability of monomer mixtures without however impairing the properties of the cured materials. Preferred stabilizers are hydroquinone monomethyl ether (MEHQ) and 2,6-di-tert.-butyl-4-methylphenol (BHT).

If the vinylcyclopropane methacrylates according to the invention are anionically or radically copolymerized with monofunctional (meth)acrylates in solution, soluble copolymers can be obtained which bear laterally-bound 2-vinylcyclopropane groups and which can be transformed in a second stage e.g. as substance film into corresponding insoluble network polymer films. The soluble copolymers and films can be used for example as radiation-crosslinkable lacquers or adhesives.

The vinylcyclopropane-(meth)acrylates according to the invention are particularly suitable for the production of dental materials, such as dental adhesives, fixing cements or filling composites, as well as materials for inlays/onlays, teeth or veneering materials for crowns and bridges.

Preferred dental materials contain:
(a) 1 to 99 wt.-%, preferably 5 to 70 wt.-% and particularly preferably 5 to 40 wt.-% of the vinylcyclopropane-(meth)acrylates according to the invention, (b) 0.01 to 5 wt.-%, particularly preferably 0.1 to 2.0 wt.-% of radical initiator, (c) 0 to 80 wt.-%, preferably 0 to 60 wt.-% and particularly preferably 0 to 50 wt.-% of other radically polymerizable monomer components, (d) 0 to 90 wt.-% filler.

The preferred level of filler depends on the intended use and is 0 to 20 wt.-% in the case of adhesives, 20 to 60 wt.-% in the case of cements and 60 to 85 wt.-% in the case of filling composites.

The dental materials according to the invention are characterized by a smaller polymerization shrinkage and good mechanical properties.

The invention is explained in more detail below with reference to embodiments.

EXAMPLES

Example 1

2-vinylcyclopropane-1,1-dicarboxylic acid monomethyl ester (3)

In a 100-ml two-necked flask with thermometer, magnet stirrer and $CaCl_2$ tube, 36.8 g (0.2 mole) of 2-vinylcyclopropane-1,1-dicarboxylic acid dimethyl ester, which is accessible from malonic acid dimethyl ester and trans-1,4-dibromobut-2-ene (cf. U.S. Pat. No. 4,713,478 and U.S. Pat. No. 4,713,479) were dissolved in 65 ml of methanol and cooled to ca. 5° C. with ice water. 13.3 g (0.2 mole) of KOH were added portionwise to the mixture, so that the temperature did not rise above 15° C. To complete the reaction, stirring was carried out for a further 12 h and the mixture was then concentrated at a rotation evaporator in vacuum (50 mbar) at 50° C. The obtained oil (ca. 43 g) was dissolved in 50 ml of water and adjusted to about pH 2–3 with conc. hydrochloric acid accompanied by cooling. The organic phase was taken up in 100 ml of diethyl ether, the aqueous phase extracted twice more each time with 100 ml of diethyl ether and the combined ether phases dried over anhydrous $Na_2SO_4$. The solution was stabilized with 0.01 g of hydroquinone monomethyl ether, concentrated in vacuum and dried in fine vacuum. 28.2 g (83% yield) of a colourless liquid were obtained.

| Elemental analysis: | $C_8H_{10}O_4$ | Calc.: C 56.47 | H 5.92 |
|---|---|---|---|
| | (170.2) | Found: C 56.60 | H 5.82 |

IR (film, $cm^{-1}$): 921 (m, sh), 1145 (s), 1209 (s, sh), 1289 (m), 1333 (s, sh), 1440 (s, sh), 1777 (s, sh), 2957 (M) and 3018 (m).

$^1$H-NMR (90 MHz, $CDCl_3$:): 1.93 and 2.03 (s, 2×1H, $CH_2$-cyclopr.); 2.88–2.90 (q, 1H, CH-cyclopr.); 3.86 (s, 3H, $CH_3$); 5.18–5.69 (m, 3H, CH=$CH_2$); 12.30 (s, 1H, COOH, H/D exch.).

$^{13}$C-NMR (75 MHz, $CDCl_3$, ppm): 171.9 and 171.7 (=O), 132.4 (<u>C</u>H=$CH_2$), 120.1 (CH=<u>C</u>$H_2$), 53.1 ($OCH_3$), 37.1 (<u>C</u>—CO), 34.2 (CH-cyclopr.) and 22.8 ($CH_2$-cyclopr.).

Example 2

2-(1-carboxymethyl-2-vinylcyclopropane-1-carboxy)-ethyl methacrylate (4)

64 g (0.31 mole) of dicyclohexylcarbodiimide were added portionwise at 0 to 10° C., accompanied by stirring, to a solution of 53 g (0.31 mole) of 2-vinylcyclopropane-1,1-dicarboxylic acid monomethyl ester, 40 g (0.31 mole) of 2-hydroxyethyl methacrylate, 1.0 g of 4-dimethylaminopyridine in 160 ml of methylene chloride. After 3 h stirring at 5° C. the formed dicyclohexylurea precipitate was filtered off and the filtrate washed with 0.5 N hydrochloric acid and then with water. After drying over anhydrous $Na_2SO_4$ the solvent was removed in water-jet vacuum and the remaining product subjected to fractional distillation in fine vacuum. 38 g (43% yield) of a colourless liquid were obtained (b.p.$_{0.2}$: 145° C.).

| Elemental analysis: | $C_{14}H_{18}O_6$ | Calc.: C 59.55 | H 6.43 |
|---|---|---|---|
| | (282.4) | Found: C 59.90 | H 6.59 | p IR (film, $cm^{-1}$): 918 (w), 1134 (m), 1168 (s), 1272 (m), 1438 (m), 1638 (w), 1726 (s) and 2956 (w).

$^1$H-NMR (400 MHz, $CDCl_3$, ppm): 1.58–1.78 (m, 2H, $CH_2$-cyclopr.); 1.95 (s, 3H, $CH_3$); 2.56–2.63 (m, 1H, CH-cyclopr.); 3.73 (s, 3H, $OCH_3$); 4.33–4.47 (m, 4H, $CH_2CH_2$); 5.11–5.48 (m, 3H, CH=$CH_2$); 5.60 and 6.13 (2s, 2H, =$CH_2$).

$^{13}$C-NMR (75 MHz, $CDCl_3$, ppm): 169.1 (a), 166.8 and 167.0 (b), 136.0 (c), 133.0 (d), 126.0 (e), 118.7 (f), 63.2 and 62.1 (g,h), 52.4 (i), 35.8 (k), 31.4 (l), 20.6 (m) and 18.3 (n).

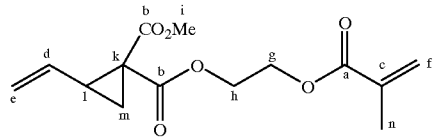

Example 3

Synthesis of 2-(1-carboxymethyl-2-vinylcyclopropane-1-carboxy)-ethyl acrylate (5)

20 g (0.10 mole) of dicyclohexylcarbodiimide were added portionwise at 0 to 10° C., accompanied by stirring, to a solution of 17 g (0.10 mole) of 2-vinylcyclopropane-1,1-dicarboxylic acid monomethyl ester, 11.6 g (0.10 mole) of 2-hydroxyethyl acrylate, 0.3 g of 4-dimethylaminopyridine in 50 ml of methylene chloride. After 3 h stirring at 5° C. the formed dicyclohexylurea precipitate was filtered off and the filtrate washed with 0.5 N hydrochloric acid and then with water. After drying over anhydrous $Na_2SO_4$ the product was chromatograph-ically purified (column: 15 cm long, diameter 2 cm, support: Silica 60, eluant: ethyl acetate/hexane: 7:3), the solvent was then removed in water-jet vacuum and the remaining product dried in fine vacuum. 19 g (70% yield) of a colourless liquid were obtained.

| Elemental analysis: | $C_{13}H_{16}O_6$ | Calc.: C 58.19 | H 6.01 |
|---|---|---|---|
| | (268.3) | Found: C 57.84 | H 6.12 |

IR (film, $cm^{-1}$): 922 (m), 988 (m), 1072 (m), 1133 (m), 1189 (s), 1271 (s), 1408 (m), 1440 (m), 1638 (m), 1730 (s) and 2955 (m).

$^1$H-NMR (400 MHz, $CDCl_3$, ppm): 1.58–1.76 (m, 2H, $CH_2$-cyclopr.); 2.57–2.63 (m, 1H, CH-cyclopr.); 3.73 (s, 3H, $OCH_3$); 4.36–4.41 (m, 4H, $CH_2CH_2$); 5.14–5.41 (m, 3H, CH=$CH_2$); 5.86–6.783 (m, 3H, CO=$CH_2$).

$^{13}$C-NMR (75 MHz, CDCl$_3$, ppm): 169.1 (a), 167.5 and 165.8 (b,c), 132.9 (d), 131.4 (e), 128.0 (f), 118.8 (g), 63.6 and 62.1 (h,i), 52.6 (j), 35.7 (l), 31.9 (m) and 20.6 (n).

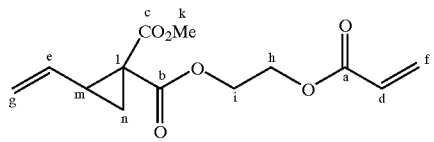

Example 4

Synthesis of 2-(1-carboxymethyl)-2-vinylcyclopropane-1-carboxy)methyl acrylic acid ethyl ester (6)

14.5 g (70 mmole) of dicyclohexylcarbodiimide were added portionwise at 0 to 10° C., accompanied by stirring, to a solution of 13 g (70 mmole) of 2-vinylcyclopropane-1,1-dicarboxylic acid monomethyl ester, 9.2 g (70 mmole) of 2-hydroxymethyl acrylic acid ethyl ester and 0.1 g of 4-dimethylaminopyridine in 40 ml of methylene chloride. After 8 h stirring at room temperature the formed dicyclohexylurea precipitate was filtered off, the filtrate washed with 0.5 N hydrochloric acid and then with water and dried over anhydrous Na$_2$SO$_4$. The product was then chromatographically purified (column: 15 cm long, diameter 2 cm, support: Silica 60, eluant: ethyl acetate/hexane: 7:3), the solvent removed in water-jet vacuum and the remaining product dried in fine vacuum. 12.4 g (62% yield) of a colourless liquid were produced.

| Elemental analysis: | C$_{14}$H$_{18}$O$_6$ (281.3) | Calc.: C 59.77 H 6.45 Found: C 59.13 H 6.27 |
|---|---|---|

IR (film, cm$^{-1}$): 2954 (m), 1729 (s), 1640 (m), 1438 (m), 1308 (m), 1228 (s) and 1029 (m).

$^1$H-NMR (400 MHz, CDCl$_3$, ppm): 5.84 and 6.36 (2 s, 2H=CH$_2$ (acrylate)), 4.80–5.29 (m, 3H, CH=CH$_2$), 4.80 and 4.96 (2 s, 2H, OCH$_2$), 3.74 (s, 3H, OCH$_3$), 2.60 (m, 1H, CH (cycloprop.)) and 1.60–1.75 (m, 2H, CH$_2$ (cycloprop.)).

$^{13}$C-NMR (75 MHz, CDCl$_3$, ppm): 14.1 (a), 23.1 (b), 31.5 (c), 35.7 (d), 52.6 (e), 60.7 (f), 63.4 (g), 119.6 (h), 127.0 (i), 132.6 (k), 135.2 (l) and 166.1–168.9 (m).

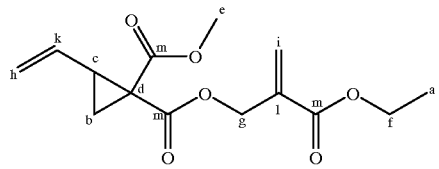

Example 5

Radical homo- and -copolymerization of 2-(1-carboxymethyl-2-vinylcyclopropane-1-carboxy)-ethyl methacrylate Homopolymerization: In a Schlenk vessel, 2.5 mol-% (relative to the monomer) of azobisisobutyronitrile (AIBN) were added to a solution of 2-(1-carboxymethyl-2-vinylcyclopropane-1-carboxy)-ethyl methacrylate (0.5 mol/l) in chlorobenzene. After degassing of the monomer solution and sealing of the Schlenk vessel under argon, the mixture was polymerized at 65° C. in a thermostatically-controlled water bath. After 4 h the polymerization was interrupted by precipitating the polymerizate by pouring the reaction mixture into 10 times the quantity of methanol. The formed polymer was filtered off and dried until the weight was constant. A homopolymer with an average molar mass of 70 000 g/mol (numerical average) was obtained in 53% yield. The $^1$H-NMR spectrum shows that the homopolymerizate is a polymethacrylate with laterally bound 1-carboxymethyl-2-vinylcyclopropane groups.

Analogously, 2-(1-carboxymethyl-2-vinylcyclopropane-1-carboxy) ethyl methacrylate was polymerized in bulk with AIBN (2.5 mol-%) at 65° C. After 15 h a transparent, hard and insoluble polymerizate was obtained in which both groups of the starting monomer that were capable of polymerization were clearly included in the polymer network formation.

Copolymerization: Analogously to the homopolymerization, a monomer mixture of 2-(1-carboxymethyl-2-vinylcyclopropane-1-carboxy)ethyl methacrylate (0.5 mol/l), methyl methacrylate (0.05 mol/l) and AIBN (2.5 mol-%) in chlorobenzene was prepared and polymerized for 2 h. The copolymer yield was 45%. The $^1$H-NMR spectrum shows that the copolymerizate contains laterally bound 1-carboxymethyl-2-vinylcyclopropane groups.

Example 6

Production of a filling composite on the basis of 2-(1-carboxymethyl-2-vinylcyclopropane-1-carboxy)-ethyl methacrylate The following composite filling materials were produced by admixing the listed components in the quantities given in Table 1 in a planetary kneader (LPM type, gap 2SP, Linde).

Material A (Comparative Example)

Composite on the basis of a mixture of two methacrylate cross-linkers [urethane dimethacrylate RM-3 (7,7,9-trimethyl-4,13-dioxo-3,14-dioxa-5,12-diazahexadecan-1,16-diyl-dimethacrylate; Ivoclar) and bis-GMA (bisphenol-A-glycidyl methacrylate; Esschem)] and a cross-linking vinyl cyclopropane [BVCPRE (bis(2-vinyl-cyclopropane-dicarboxylic acid methyl) resorcinyl ester; Ivoclar)].

Material B

In composite B, some of the vinylcyclopropane BVCPRE was replaced by the vinylcyclopropane methacrylate according to the invention (4).

In order to examine the mechanical properties, testpieces were formed according to ISO standard 4049 (1988) and cured by irradiation with a dental light source (Vivadent Spectramat; wavelength 400 to 500 nm; 2×3 minutes). The mechanical properties were then determined according to ISO standard 4049. To determine the release of BVCPRE, analogously produced testpieces (diameter: 10 mm; height: 2 mm) were stored in 20 ml of ethanol at 37° C. in an agitator and the elutable residual monomer content of BVCPRE was ascertained by means of HPLC after 72 h.

TABLE 1

Composition of the filling composites

| Constituent | Material A (comparative example) (wt.-%) | Material B (wt.-%) |
|---|---|---|
| Urethane dimethacrylate RM-3 | 7.47 | 7.47 |
| bis-GMA | 8.38 | 8.38 |
| BVCPRE[1] | 4.00 | 3.00 |
| Vinylcyclopropane methacrylate (4) | — | 1.00 |
| Photoinitiator[2] | 0.18 | 0.18 |
| Ytterbium trifluoride[3] | 12.82 | 12.82 |
| Aerosil OX-50, sil.[4] | 1.03 | 1.03 |
| Ba-Glas, sil.[5] | 52.40 | 52.40 |
| Sphärosil, sil.[6] | 13.72 | 13.72 |

[1] Synthesis cf.: EP 0 798 286 A1
[2] Initiator: camphor quinone; accelerator: N-(2-cyanoethyl)-N-methyl-aniline; inhibitor: hydroquinone monomethyl ether
[3] Ytterbium fluoride (Rhone-Poulenc)
[4] Silanized pyrolysis silica (Degussa)
[5] Silanized barium aluminium silicate glass powder (Schott)
[6] Silanized $SiO_2$—$ZrO_2$ mixed oxide (Tokoyama Soda)

TABLE 2

Properties of the composites

| Material property | Material A (Comparative example) | Material B |
|---|---|---|
| Bending strength according to ISO 4049 (MPa) | 112 | 108 |
| Bending E-modulus according to ISO 4049 (GPa) | 8800 | 10600 |
| Elutable BVCPRE content (%) | 0.203 | 0.094 |

It is clear from Table 2 that material B with the vinylcyclopropane methacrylate (4) according to the invention is characterized by its significantly better cross-linking, which can be derived on the one hand from the higher E-modulus and on the other from the clearly smaller elutable BVCPRE residual monomer content.

What is claimed is:

1. The vinylcyclopropane derivative according to the formula:

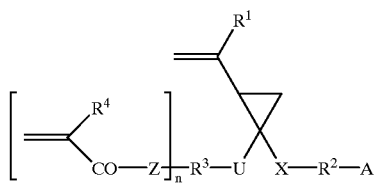

(I)

in which

A is —(—Y—CO—C(=$CH_2$)$R^4$)$_m$ or —C(=$CH_2$)CO—O—$C_{1-4}$-alkyl;

U, X stand for CO, COO or CONH;

Y, Z stand for O or NH or are absent, but Y and Z cannot be absent at the same time when A is —(—Y—CO—C(=$CH_2$)$R^4$)$_m$;

n, m stand for an integer from 0 to 4, but n and m are not 0 at the same time;

$R^1$ is H, $CH_3$ or Cl;

$R^2$, $R^3$ stand for H, a $C_1$- to $C_{10}$-alkyl or alkylene radical, which can be interrupted by O, S or NH, for a $C_6$- to $C_{14}$-aryl or arylene, $C_7$- to $C_{14}$-alkylaryl or alkylarylene or a $C_5$- to $C_8$-cycloalkyl or cycloalkylene; and $R^4$ is H or a $C_1$- to $C_{10}$-alkyl.

2. The vinylcyclopropane derivative according to claim 1, wherein

U, X stand for COO or CONH,

Y, Z stand for O or are absent, n, m stand for an integer from 0 to 2, $R^1$ stands for H, $R^2$, $R^3$ stand for a $C_1$- to $C_6$-alkyl or alkylene radical, $C_6$-aryl or arylene or a $C_6$-cycloalkyl or cyclo-alkylene radical; and/or $R^4$ is H or a $C_1$–$C_3$-alkyl radical.

3. The vinylcyclopropane derivative according to claim 2, wherein $R^2$ and $R^3$ are the same;

$R^4$ is H;

n, m are in each case 1 and

U, X stand for COO or CONNH, or $R^2$ and $R^3$ are different;

N is 0,

M is 1 or 2,

Z is absent,

Y stands for O and $R^4$ stands for H.

4. A process for the production of vinylcyclopropane derivatives according to claim 1, wherein a vinylcyclopropane derivative of formula I, in which $R^2$ is a $C_1$- to $C_{10}$-alkyl or phenyl radical, is reacted with a (meth)acrylic acid derivative, having, as a leaving group, OH or halogen, to give the intermediate stage (IV) or the final stage (V), and (IV) is optionally converted with a further (meth)-acrylic acid derivative (III), which can be identical with the first (meth)acrylic acid derivative, into the desired vinylcyclopropane derivative of formula I.

5. A dental material containing (a) 1 to 99 wt.-% of a vinylcyclopropane derivative according to claim 1, (b) 0 to 80 wt.-% of another radically polymerizable polymer, (c) 0.01 to 5 wt.-% of an initiator for the radical polymerization, (d) 0 to 90 wt.-% of a filler.

6. A dental material according to claim 5, containing (a) 5 to 70 wt.-% of the vinylcyclopropane derivative, (b) 0 to 60 wt.-% of another radically polymerizable polymer, and/or (c) 0.1 to 2 wt.-% of an initiator for the radical polymerization.

7. A dental material according to claim 5, containing 0 to 20 wt.-% of an adhesive, 20 to 60 wt.-% of a cement or 60 to 85 wt.-% of a filling composite filler.

8. A dental adhesive comprising the vinylcyclopropane derivative of claim 1.

9. A dental cement comprising the vinylcyclopropane derivative of claim 1.

10. A dental composite comprising the vinylcyclopropane derivative of claim 1.

11. A dental moulding comprising the vinylcyclopropane derivative of claim 1.

* * * * *